(12) United States Patent
Muchovej et al.

(10) Patent No.: US 8,278,248 B1
(45) Date of Patent: Oct. 2, 2012

(54) MYCOHERBICIDE FOR CONTROLLING COGONGRASS

(75) Inventors: James J. Muchovej, Lloyd, FL (US); Oghenekome U. Onokplse, Tallahassee, FL (US)

(73) Assignee: Florida Agricultural and Mechanical University, Tallahassee, FL (US)

( * ) Notice: Subject to any disclaimer, the term of this patent is extended or adjusted under 35 U.S.C. 154(b) by 0 days.

(21) Appl. No.: 13/163,987

(22) Filed: Jun. 20, 2011

(51) Int. Cl.
*A01N 63/00* (2006.01)
*C12N 1/00* (2006.01)
(52) U.S. Cl. .................................. 504/117; 435/254.1
(58) Field of Classification Search .................. None
See application file for complete search history.

(56) References Cited

U.S. PATENT DOCUMENTS

| | | |
|---|---|---|
| 4,606,751 A | 8/1986 | Van Dyke et al. |
| 5,332,573 A | 7/1994 | Yamaguchi et al. |
| 5,434,121 A | 7/1995 | Gohbara et al. |
| 5,498,591 A | 3/1996 | Gohbara et al. |
| 5,498,592 A | 3/1996 | Gohbara et al. |
| 6,172,003 B1 | 1/2001 | Yamaguchi et al. |
| 6,265,347 B1 | 7/2001 | Chandramohan et al. |

OTHER PUBLICATIONS

Yandoc et al. "Suppression of cogongrass (*Imperata cylindrica*) by a bioherbicidal fungus and plant competition", Weed Science, 52:649-653 (2004).
Farr et al. "Fungi on Plants and Plant Products in the United States", APS Press, St. Paul, MN (1989).
Smalls, Rahsirearl D. "Pathogenicity and Severity of Leaf Spot Fungi on Cogongrass", Thesis (2007.
Alfieri, Jr. et al. "Diseases and Disorders of Plants in Florida", FL Dept of Agriculture and Consumer Affairs, Bulletin No. 14 (1994).

*Primary Examiner* — Alton Pryor
(74) *Attorney, Agent, or Firm* — Parks IP Law LLC; Collen A. Beard

(57) ABSTRACT

A newly discovered fungus *Bipolaris imperatae* which possesses herbicidal effects on grassy weed species such as cogongrass (*Imperata cylindrica*), methods of applying *Bipolaris imperatae* fungus as a mycoherbicide to control growth of cogongrass and similar wild grassy weeds, and compositions containing an effective amount of *Bipolaris imperatae* fungus and an agriculturally acceptable carrier to control growth of cogongrass and similar weeds.

8 Claims, No Drawings

MYCOHERBICIDE FOR CONTROLLING COGONGRASS

FIELD OF THE INVENTION

The present invention relates to a previously undescribed species of fungus named *Bipolaris imperatae* and deposited in the ARS Patent Culture Collection (NRRL) and methods and compositions for weed control using the new species.

BACKGROUND OF THE INVENTION

Weeds are a tremendous problem of farmers and growers throughout the world. For example, it has been reported that cogongrass (*Imperata cylindrica*) is one of the ten worst weeds worldwide and has become firmly established in the Southeastern United States, especially in areas where tillage is not the principle method of weed control. Cogongrass grows best in relatively acidic soils that are low in fertility and highly leached.

To date the only fungi reported on hosts in the genus *Imperata* in the United States are two species of rust found on *Imperata brevifolia* Vasey in Arizona. Farr et al., Fungi on Plants and Plant Products in the United States, APS Press, St. Paul, Minn. (1989). There is no listing of the genus *Imperata* as a host of fungus in the state of Florida. Alfieri S A Jr. et al., Diseases and Disorders of Plants in Florida, Division of Plant Industry Bulletin 14, Gainesville (1994). In international lists of agriculturally important fungi, *Imperata cylindrica* is either not listed or is listed with only rust species. Viegas, Indite de Fangos da America do Sol, Instituto Agronomico, Campinas, Brazil (1961).

Current methods of controlling cogongrass include chemicals and mechanical practices, such as disking, mowing, and burning. However, the most widely used weed control practice is the use of chemical herbicides which poses ecological concerns of introducing toxic and sometimes non-biodegradable substances into the ecosystem. Other issues with use of chemical herbicides include lack of residual control, injury to non-target organisms, undesirable residues in harvested products, and carryover in subsequent crops.

A more recently used practice for managing cogongrass is the use of native grass species to compete with cogongrass. While use of native grass as a biocontrol is important both environmentally and biologically, it has been observed that the use of native grass species as a biocontrol in the short term is slow and less effective when compared to chemicals and less certain when compared to chemical and mechanical control practices.

In light of the concerns with chemical herbicides, there is a demand for biological control methods. In the field of herbicides, extensive investigations have been carried out on biologically based herbicides, such as mycoherbicides, which use a fungus that is pathogenic to the weed. For example, U.S. Pat. No. 4,606,751 to Van Dyke et al., teaches using the fungus *Bipolaris sorghicola* as a mycoherbicide to control Johnson grass (*Sorghum halepense*). However, there are no bioherbicides yet available against cogongrass.

With the foregoing in mind, it is an object of the present invention to provide bioherbicide methods and compositions for controlling cogongrass and similar wild grassy weeds.

SUMMARY OF THE INVENTION

The present invention concerns methods and compositions useful in weed control. More specifically, the subject invention concerns a new fungal species *Bipolaris imperatae* and use of the fungus to provide enhanced control of cogongrass (*Imperata cylindrica*).

In another embodiment, the invention relates to methods of using the fungus *Bipolaris imperatae* to provide enhanced control of cogongrass.

In a further embodiment, the invention relates to mycoherbicide compositions for weed control, comprising an effective amount of the fungus *Bipolaris imperatae* and an agriculturally acceptable carrier.

In yet another embodiment, the invention relates to a biologically pure culture of the fungus *Bipolaris imperatae*, a lyophilized culture of which has been deposited in accordance with the Budapest treaty at the ARS Patent Culture Collection (NRRL) on May 18, 2011 and assigned NRRL 50513.

DETAILED DESCRIPTION

A previously undescribed species of *Bipolaris* has been discovered and named *Bipolaris imperatae*. The species was discovered on cogongrass (*Imperata cylindrical*) and is pathogenic to cogongrass. The fungus is relatively non-pathogenic to other plant species of native and amenity grasses and therefore is useful as a mycoherbicide against cogongrass. *Bipolaris imperatae* may be effective when formulated for this use in agricultural crops. Since this biological organism is part of the natural ecosystem, i.e. it is readily isolated from cogongrass, it does not present ecological problems like chemical herbicides.

Fungi were isolated from naturally occurring lesions on wild cogongrass plants. The fungi were identified using illustrated keys. Three isolates, termed JJ1, JJ2 and JJ3, did not key to existing fungi and were further explored. These isolates were used for pathogenicity and host range testing. The isolates were pathogenic to *Imperata cylindrica* (cogongrass), but were relatively non-pathogenic to other plant species of native and amenity grasses.

Description of the Isolated Fungus

Leaf spots were light brown and 1-2 cm wide and 2-3 cm in length. Condiophores were elongate and geniculate at the apex. Condiogenic cells were integrated, terminal, polyblastic, and cicatrized. Conidia were pale brown, smooth, concolorous, cylindrical, flexuous, and all cells were approximately the same size, 39-130×8.7-13 µm, and were (3) 7-8 (12) distoseptate. The hilum was on the inside of the curve, 2 µm in width. Germination was by a germ tube that was sub hilar. The largest cell is often just above the basal cell. Septa formed with the first septum median, the second septum is apical to the first, and the third septum delineates the basal cell.

Uses for the Fungus

The compositions and methods of the invention include the provision of sufficient spores of *Bipolaris imperatae* to produce a sufficient amount of a mycoherbicide for application to the undesired cogongrass. The spores may be obtained by isolated the fungus from diseased cogongrass plants or from cultivated fungus.

Mycoherbicide compositions may be prepared as a liquid formulation by suspending the spores in an agriculturally acceptable carrier for application to the undesired cogongrass or the location where it is growing (situs).

For compositions of the invention, any agriculturally acceptable carrier can be used whether it is liquid or solid as long as it can be employed in agricultural or horticultural formulations and is preferably biologically inert. Exemplary agriculturally acceptable liquid carriers include, but are not limited to, water, surfactants, vegetable oils, and mineral oils.

In a preferred embodiment, the agriculturally acceptable carrier for a liquid formulation is water, and the mycoherbicide has a spore concentration of greater than $1\times10^4$ spores per ml, more preferably greater than $1\times10^6$ spores per ml.

Mycoherbicide compositions can also be prepared as granular formulations, flowable formulations, or wettable powder formulations by mixing the spores with an agriculturally acceptable carrier, which is then applied to the undesired host vegetation or situs.

Suitable agriculturally acceptable solid carriers include mineral powders, such as clay, talc, bentonite, calcium carbonate, diatomaceous earth and white carbon; vegetable flours such as soybean flour and starch, and some polymers such as polyvinyl alcohol and polyalkylene glycol.

A method of controlling wild grassy weeds includes applying the mycoherbicide containing *Bipolaris imperatae* to the undesired host vegetation, i.e., cogongrass, to be controlled. The mycoherbicide can be applied by spraying a spore containing solution of *Bipolaris imperatae* onto the cogongrass or situs in an amount sufficient to coat the leaves of the cogongrass. One application may be sufficient to reduce current growth; however, repeat applications may be necessary if regrowth of the plant occurs from resistant or below ground structures. Also the method of the present invention may be used in addition to or in conjunction with other control measures.

The invention is further described in connection with the following non-limiting examples.

Example 1

Discovery of the Fungus

Cogongrass from a natural infestation in Leon County, Florida was collected and analyzed for the presence of leaf spot fungi. Diseased leaf tissue was excised and surface sterilized. The segment of leaf tissue was immersed in 50% isopropanol for one minute and then placed in 2% aqueous sodium hypochlorite for one minute. The tissue was transferred to sterilized tap water for 30-40 seconds and then placed on potato dextrose agar (PDA) in a Petri plate. The plates were incubated at room temperature until fungi appeared and then transferred to PDA slants for storage at 5° C.

A wet mound of the isolated fungi was made in water, on a glass microscope slide and then covered with a cover slip. The fungi were observed using a compound microscope (Wolfe Digivu TM CVM) and were photographed using the program Motic Images 2000 1.3. Characteristics recorded included length, width, color, shape, and number of septa. Size of the conidia was determined using a movable wire ocular micrometer. Fungi were identified using illustrated keys. Barnett et al., Illustrated Genera of Imperfect Fungi, 4$^{th}$ Edition, APS Press, St. Paul, Minn. (1998).

A majority of the fungi isolated were "common" fungi that are often associated with leaf spots on grasses. However one fungus was unable to be keyed to known fungi. In trying to classify this organism to species, it keyed close to *Bipolaris ocella* (Faris) Shoemaker, *B. melinidis* Alcorn, or *B. curvispora* El-Shafie (Muchovej et al., Fitopatologia brasileira 13:211-223, 1988); to *Exserohilum paspali* Muchovej & Nesio (Sivanesan, Mycological Papers 158, 1987); to *B. euphorbiae* (Hansford) Muchovej & A. O. Carvalho; to *B. sacchari* (Butler) Shoemaker or *B. setariae* (Saw.) Shoemaker.

Both *B. curvispora* and *B. melinidis* have been determined to be co-specific and have been reduced to synonymy of *Bipolaris saiviniae* (Muchovej) Alcorn. *B. salviniae* has distinctly curved conidia that are 75-205×10-18 µm. The curved conidia and the longer length are distinctly different from our species. *Exserohilum paspali* was later determined to be *Bipolaris micropus* (Dreschsler) Shoemaker. This species has a distinct protuberant hilum that our species does not have. *B. euphorbiae* has conidia that are mostly slightly curved, usually thickest near the middle and tapering towards the rounded ends, pale to mid-golden brown, 5-11 distoseptate, 50-130×11-17 µm, hilum 2.5-4 µm wide. This species is pathogenic on *Euphorbia*, which is not a type of grass.

*B. sacchari* (Butler) Shoemaker [syn: *Bipolaris ocella* (Faris) Shoemaker fide Sivanesan (1987)] has conidia that are slightly curved, rarely straight, cylindrical or narrowly ellipsoidal, that are mid pale to mid yellow golden brown, 5-9 distoseptate and 35-96×9-17 µm. There are several differences with our species including width of the conidia and color. *B. sacchari* is pathogenic on *Saccharum, Cynodon, Panicum* and *Pennisetum*.

*B. setariae* (Saw.) Shoemaker has conidia that are slightly curved, rarely straight, fusoid or navicular, pale to mid golden brown, smooth, 5-10 distoseptate, 45-100×1015 µm. This species may be the closest morphologically, but our species was narrower. Also, *B. setariae* is pathogenic to a host of grasses including *Setaria, Echiniochloa, Eleusine, Eragrostis, Panicum*, and *Pennisetum*.

Example 2

Host Range on Various Grasses

Production of Conidia

Various isolates of the newly discovered fungus were collected from different locations in the Leon County area, and these were then used for pathogenicity testing.

For the production of conidia, each isolate was cultured on either potato dextrose agar (Tuite, Plant Pathological Methods, Burgess Publishing, Minneapolis, Minn. (1969)) or a chemically defined medium (Muchovej, Annals Applied Biology, 109, 249-258 (1986)) in Petri dishes for seven to fourteen days. Conidia were harvested by flooding with sterile water and dislodging conidia with a sterile cotton swab. The resultant suspension was filtered through a double layer of cheesecloth and used as inoculum. Inoculum was prepared fresh for each inoculation.

Potential Host Plants

Grasses tested included cogongrass, centipede (*Eremochloa ophiuroides* (Munro) Hack.), St. Augustine (*Stenotaphrum secundalum* (Walt.) Kuntze), Bermuda grass (*Cynodon dactylon* (L.) Pers.), Bahiagrass (*Paspalum notatum* Flugge), muhlygrass (*Muhlenbergia capillaris* (Lam.) Trin.), switchgrass (*Panicum virga tum* L) "Miami", and maidencane (*Panicum hemitomon* Schult.) "Citrus". All plants were grown in 20 cm pots containing a greenhouse soil mixture of 10% peat; 10% sand and 80% pine bark (Graco Fertilizer Co, Cairo, Ga.).

Plants had a minimum of 5 leaves and had been established for more than a month. Plants were sprayed with aqueous suspensions of spores using a hand-held mist sprayer. The inoculated plants then were subjected to 100% RH using an ultrasonic humidifier (Holmes HM-460B, 8.4 l d$^{-1}$ output). The inoculation chamber, situated on a greenhouse bench, was 2.4×1.2×1.2 m (l:w:h) in size and covered with a plastic sheet. The humidifier was placed inside of the chamber and allowed to mist continuously for 24 hr. At that time, the humidifier was removed but the plastic chamber was left in place for an additional 24 hr. One of each set of plants was inoculated and there was one set of uninoculated controls. After 2-3 days, the plants were returned to the greenhouse and evaluated for development of leaf spots for up to 7 days.

Lesions were dark brown to black and circular with length and width of approximately 1-2 mm. The JJ1 isolate was pathogenic to cogongrass, switchgrass and maidencane, while the JJ2 and JJ3 isolates were only pathogenic to cogongrass.

Example 3

Severity of Fungal Pathogenicity

Once pathogenicity of the isolates to cogongrass was established, the isolates of *Bipolaris imperatae* were subjected to disease severity tests. Inoculum was prepared as stated in Example 2. Conidial densities were measured with the aid of a haemacytometer. If a more diluted suspension was required an aliquot of the suspension was added to sterile water. If a more concentrated suspension was needed, the suspension was centrifuged and then decanted. Formulations having spore concentrations between $1\times10^4$ and $7\times10^6$ spores per ml were prepared as a suspension in water from three *Bipolaris imperatus* isolates.

Cogongrass plants were prepared as above. One concentration of each isolate liquid formulation prepared was inoculated onto non-diseased cogongrass plants. There was also one set of uninoculated control plants. The cogongrass plants were sprayed with 10 ml of each formulation using a hand-held mist sprayer. The cogongrass plants were then placed on a bench and covered with a plastic sheet and the humidity adjusted to 100% relative humidity (RH), using an ultrasonic humidifier, for 24 hours. The humidifier was then removed; however the plastic sheet was left in place for an additional 24 hours. After 2 days, the cogongrass plants were returned to the greenhouse and evaluated for development of leaf spots for up to 7 days.

A disease severity scale was used to determine the severity of each fungal pathogen tested. The leaves of the cogongrass plants were observed and ranked according to the percent of lesion coverage on each of the leaves. The number of lesions per $cm^2$ on the surface on the leaves was determined by randomly placing a 1 $cm^2$ template over the leaves and counting the number of lesions found within. Any part of a lesion that was found inside of the area was counted as a lesion.

Table 1 describes the numerical values assigned for severity of disease.

TABLE 1

| | |
|---|---|
| 0 | No disease-no lesion |
| 1 | 0.1-0.5% of leaf surface decreased (only a few longitudinal lesions with or without chlorotic margins) |
| 2 | 5-10% of leaf surface diseased (several lesions on the leaf surface) |
| 3 | 15-30% of leaf surface diseased (many longitudinal lesions on the leaf lamina) |
| 4 | 45-55% of leaf surface diseased (many lesions with some coalescing) |
| 5 | Over 75% of the leaf surface diseased (many coalesced lesions on the leaf lamina with some wilted zones) |

Table 2 below lists the disease severity for three different *Bipolaris imperatae* isolates inoculated onto cogongrass plants. All three of the isolates provided lesions on cogongrass plants.

JJ1 and JJ2 isolates showed no lesions at conidial concentrations of $1\times10^4$ conidia/ml but began to show pathogenicity at $1\times10^5$ conidia/ml. Leaf spots were produced by JJ3 at all concentrations tested. For isolates JJ1 and JJ2, there was minimal or no increase in disease severity with increasing concentrations; however, with the isolate JJ3 there was a noticeable increase in disease with increased concentration of conidia. The concentration of $7\times10^6$ conidia/ml produced over 15% leaf area coverage. Disease occurrence was observed on 22 leaves at this concentration. The increase in pathogenicity was in both the amount of lesions found on plants and the number of leaves that had lesions. The highest concentration gave severe levels of disease. NT means not tested and "n" is the number of diseased leaves at each concentration of inoculum.

TABLE 2

| Isolate | Concentration (conidia per ml) | | | | |
|---|---|---|---|---|---|
| | $1 \times 10^4$ | $1 \times 10^5$ | $1 \times 10^6$ | $3.3 \times 10^5$ | $7 \times 10^6$ |
| *Bipolaris Imperatae* JJ1 | 0 (n = 0) | 0.5 (n = 1) | NT | NT | NT |
| *Bipolaris Imperatae* JJ2 | 0.64 (n = 7) | 0.75 (n = 6) | NT | 0.69 (n = 8) | 0.5 (n = 3) |
| *Bipolaris Imperatae* JJ3 | 0.5 (n = 2) | 0.96 n = 14) | 1.98 (n = 20) | NT | 3.29 (n = 24) |

It should be understood that the examples and embodiments described herein are for illustrative purposes only and that various modifications or changes will be suggested to persons skilled in the art and are to be included within the spirit and purview of this application and the scope of the appended claims.

The invention claimed is:

1. A method of selectively controlling cogongrass (*Imperata cylindrica*), wherein said method comprises applying an effective amount of the fungus *Bipolaris imperatae* to said cogongrass;
   wherein the *Bipolaris imperatae* has the characteristics of ARS Patent Culture Collection (NRRL) number 50513.

2. The method of claim 1, wherein the fungus *Bipolaris imperatae* is applied to the cogongrass as a spray.

3. The method of claim 1, wherein the fungus *Bipolaris imperatae* is applied to the cogongrass as an aqueous solution.

4. The method of claim 1, wherein the fungus *Bipolaris imperatae* is applied to the cogongrass as a suspension of spores having a concentration of greater than $1\times10^4$ spores per milliliter.

5. A mycoherbicide composition comprising an effective amount of *Bipolaris imperatae* and an agriculturally acceptable carrier;
   wherein the *Bipolaris imperatae* has the characteristics of ARS Patent Culture Collection (NRRL) number 50513.

6. The mycoherbicide composition of claim 5, wherein the agriculturally acceptable carrier is water.

7. The mycoherbicide composition of claim 5, wherein the composition is a suspension of *Bipolaris imperatae* spores having a concentration of greater than $1\times10^4$ spores per milliliter.

8. A biologically pure culture of the fungus *Bipolaris imperatae* having the characteristics of ARS Patent Culture Collection (NRRL) number 50513.

\* \* \* \* \*